United States Patent  
Zribi et al.

(10) Patent No.: US 7,428,055 B2  
(45) Date of Patent: Sep. 23, 2008

(54) INTERFEROMETER-BASED REAL TIME EARLY FOULING DETECTION SYSTEM AND METHOD

(75) Inventors: Anis Zribi, Rexford, NY (US); Min-Yi Shih, Carson City, NV (US); Guiju Song, Shanghai (CN); Ajit Achuthan, Niskayuna, NY (US); Glenn Scott Claydon, Wynantskill, NY (US); Stacey Joy Kennerly, Niskayuna, NY (US); Kuna Venkat Satya Rama Kishore, Bangalore (IN); Jianming Zheng, Shanghai (CN); Kevin George Harding, Niskayuna, NY (US); Hua Xia, Altamont, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 11/538,885

(22) Filed: Oct. 5, 2006

(65) Prior Publication Data

US 2008/0084565 A1 Apr. 10, 2008

(51) Int. Cl.  
*G01B 9/02* (2006.01)  
*G01N 21/43* (2006.01)  
(52) U.S. Cl. ........................ 356/481; 356/517  
(58) Field of Classification Search ................. 356/451, 356/477, 481, 517  
See application file for complete search history.

(56) References Cited

U.S. PATENT DOCUMENTS

| | | | | |
|---|---|---|---|---|
| 5,082,629 A | * | 1/1992 | Burgess et al. | 422/82.11 |
| 5,187,545 A | * | 2/1993 | Allgauer | 356/482 |
| 5,383,467 A | * | 1/1995 | Auer et al. | 600/342 |
| 5,760,391 A | * | 6/1998 | Narendran | 250/227.14 |
| 5,982,962 A | * | 11/1999 | Koops et al. | 385/37 |
| 6,233,746 B1 | * | 5/2001 | Skinner | 250/227.18 |
| 6,239,876 B1 | * | 5/2001 | Brandenberg | 356/481 |
| 6,275,628 B1 | * | 8/2001 | Jones et al. | 385/29 |
| 6,295,130 B1 | * | 9/2001 | Sun et al. | 356/454 |
| 6,493,090 B1 | * | 12/2002 | Lading et al. | 356/484 |
| 6,519,037 B2 | * | 2/2003 | Jung et al. | 356/419 |
| 6,564,087 B1 | * | 5/2003 | Pitris et al. | 600/478 |
| 6,580,510 B2 | * | 6/2003 | Nawracala | 356/451 |
| 7,104,331 B2 | * | 9/2006 | Bussear et al. | 166/373 |
| 2002/0021450 A1 | * | 2/2002 | Aoki | 356/499 |
| 2005/0254061 A1 | * | 11/2005 | Alphonse | 356/479 |

* cited by examiner

*Primary Examiner*—Patrick Connolly  
*Assistant Examiner*—Scott M Richey  
(74) *Attorney, Agent, or Firm*—Shawn A. McClintic (57) ABSTRACT

A interferometer-based fouling detection system and method are described. The system may include a fiber optic cable, a light source in communication with the fiber optic cable, at least one photo detector in communication with the fiber optic cable, and at least one interferometric spectrometer. The fiber optic cable may include a long period grating and a fiber Bragg grating or it may include a facet edge. The system may instead include a fiber optic cable, a light source in communication with the fiber optic cable, at least one photo detector in communication with the fiber optic cable, a fiber coupler, a reference probe including a mirror, a sample probe, and an interferometer.

9 Claims, 10 Drawing Sheets

INTERFEROMETER-BASED REAL TIME EARLY FOULING DETECTION SYSTEM AND METHOD

BACKGROUND

The invention relates generally to fouling detectors, and more particularly to interferometer-based fouling detectors.

Fouling is the nucleation and growth of biological, organic or inorganic, deposits on a substrate. The substrate can be a surface of an implantable device in a biological system, the wall of heat exchanger tubing or cooling tower, or the walls and trays of a fractionation tower, for example. Fouling typically results in a degradation of the performance of such systems, high maintenance costs, and the potential need for replacement of either damaged portions or the entire system. For example, in reverse osmosis systems, replacement costs of membranes represents nearly thirty percent of the cost of operation of such a system. Membrane fouling in reverse osmosis systems is usually a combination of colloid build up, inorganic scale, and bio-film resulting in irreversible damage to the membranes. In reverse osmosis systems, fouling is affected by numerous factors, such as, for example, the quality of the incoming water, the temperature of the water, the water flow rate, the slat ions concentration gradients across the membrane, and the initial quality of the membrane.

The occurrence of fouling is difficult to predict sufficiently early enough to inhibit damage to membranes. Such difficulty is further exacerbated due to the lack of control of the incoming water quality, which inhibits the possibility to actively adjust membrane pretreatment chemical dosage to slow fouling growth without using excessive amounts of cleaning chemicals.

Heat exchangers and cooling towers are other examples where fouling consequences may be serious. Removal of severe fouling in a $DeC_3$ reboiler, for example, is a challenging, time consuming, and expensive endeavor. Often, such removal leads to costly system shut downs and large energy losses.

It is therefore desirable to develop sensing technology which enables closed loop monitoring and treatment of fouling at early stages, i.e., prior to the thickness of fouling deposits reaching 10 micrometers.

BRIEF DESCRIPTION

The invention includes embodiments that relate to a system for detecting a fouling layer within a vessel, or on top of a surface exposed to chemicals and biological media. The system includes a fiber optic cable, a light source in communication with the fiber optic cable, at least one photo detector in communication with the fiber optic cable, and an interferometric spectrometer in communication with the fiber optic cable. The interferometric spectrometer is adapted to detect the fouling layer by tracking a change of refractive index induced by the fouling layer.

The invention includes embodiments that relate to a coherent interferometer-based system for detecting a fouling layer. The system includes a fiber optic cable, a light source in communication with the fiber optic cable, and at least one photo detector in communication with the fiber optic cable. The system also includes a fiber coupler, a reference probe including a mirror, a sample probe, and an interferometer in communication with the fiber optic cable and adapted to scan the mirror of the reference probe to obtain a reflectivity profile of the fouling layer.

The invention includes embodiments that relate to a method for detecting in real-time fouling within a vessel. The method includes providing a probe in optical communication with an area of the vessel susceptible to fouling, inputting light to the probe, detecting light from the probe, detecting a reference light signal, and analyzing interference between the light from the probe and the reference light signal.

These and other advantages and features will be more readily understood from the following detailed description of preferred embodiments of the invention that is provided in connection with the accompanying drawings.

DETAILED DESCRIPTION

The invention includes embodiments that relate to interferometer-based fouling detection systems and methods.

Figure 1:
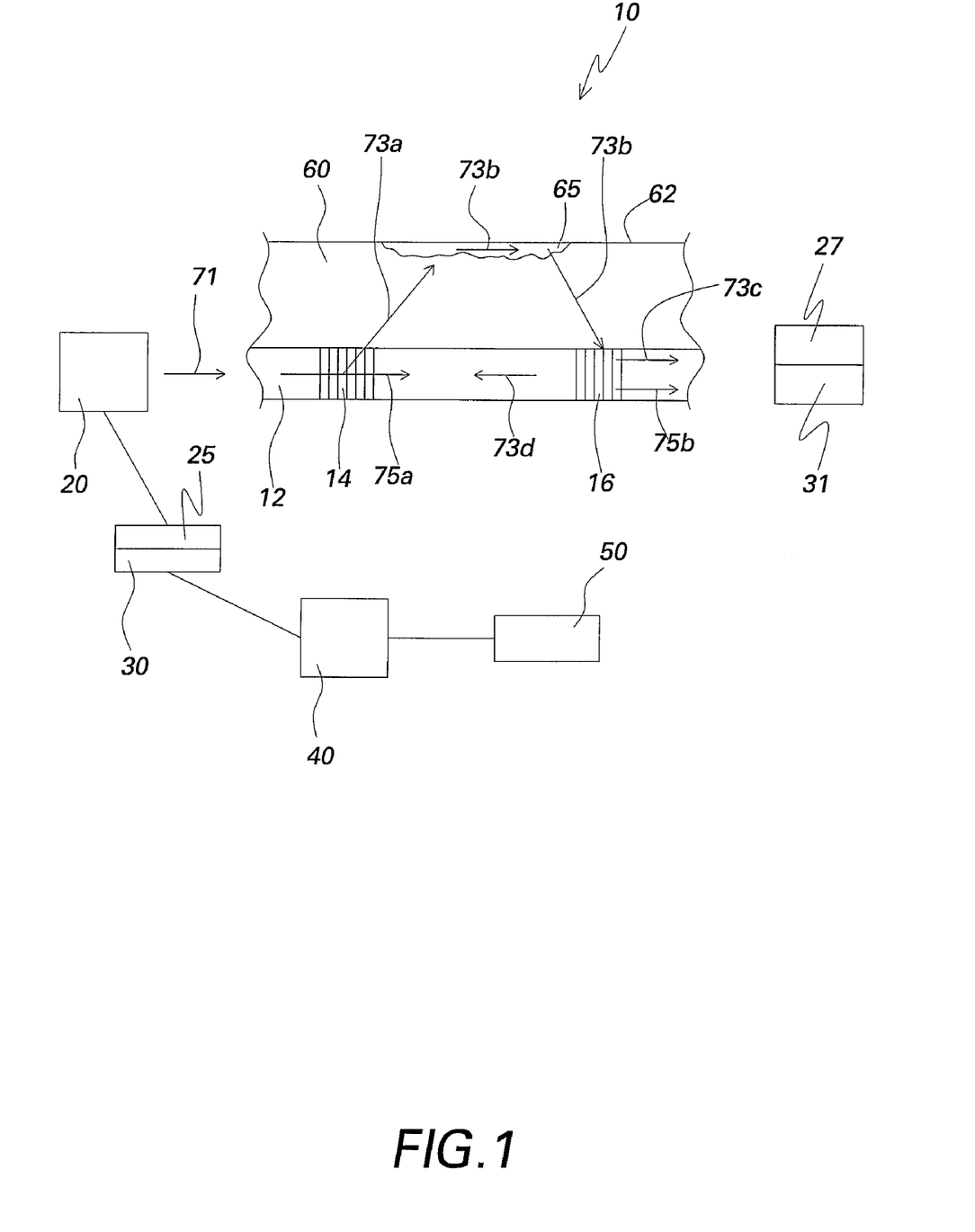
FIG. 1 is a schematic depiction of an interferometer-based system constructed in accordance with an embodiment of the invention.

With particular reference to FIG. 1, there is shown a fouling inspection system 10 that includes a fiber optic cable 12, a light source 20, an interferometric spectrometer 25, photo detectors 30 and 31, signal conditioning circuitry 40, and a central processing unit 50. The fiber optic cable 12 serves as a probe to be inserted within a vessel that may, due to its function, be susceptible to fouling. Examples of vessels for which the fouling inspection system 10 may be useful in ascertaining fouling include biological systems, heat exchangers, cooling towers, fractionation towers, boilers, reboilers, debutanizer, and depropanizers.

A long period grating 14 is disposed within the fiber optic cable 12. Further, a fiber Bragg grating 16 is disposed within the fiber optic cable 12 in series with the long period grating 14. The light source 20 outputs light signals into the fiber optic cable 12. The light signals are split into various portions. Specifically, the light signals are split at the long period grating 14 and a portion leaks into the cladding and is directed to the fiber Bragg grating 16. The fiber Bragg grating 16 partially reflects some of that portion back to the long period grating 14. The reflected portion, having been transmitted twice through the long period grating 14, is analyzed using an interferometric spectrometer 25, such as a Fabry Perot, and the photo detector 30. The interferometric spectrometer 25 and the photo detector 30 may be integrated into a commercially available fiber-optic interrogation system, such as one manufactured by Micron Optics Inc.

More specifically, the light source 20 outputs light signals, such as light signal 71. The light source 20 may be a tunable laser. As the light signal 71 is transmitted through the fiber optic cable 12, the signal 71 is split into two portions. The first portion 73a leaks out of the sensor core of the fiber optic cable 12 into the fiber grating cladding 60. The second portion 75a continues through the fiber optic cable 12. The first portion 73a is transmitted through any fouling layer 65 on the exterior wall 62 of the fiber grating cladding 60. While in the fouling layer 65, the first portion 73a is altered, and the altered first portion signal 73b is transmitted back into the fiber optic cable 12. The altered first portion 73b is transmitted through the fiber Bragg grating 16, and a filtered first portion signal 73c is output. The second portion 75a is also transmitted through the fiber Bragg grating 16, outputting a filtered second portion signal 75b. The fiber Bragg grating 16 effectively reflects a fouling induced transmission signal back to an interrogation system twice, hence enabling a sensing probe to function in a reflection-based design. Additionally, a portion 73d of the second portion signal 75a is reflected back along the fiber optic cable 12 toward the light source 20, the interferometric spectrometer 25, and the photo detector 30.

Figure 3:
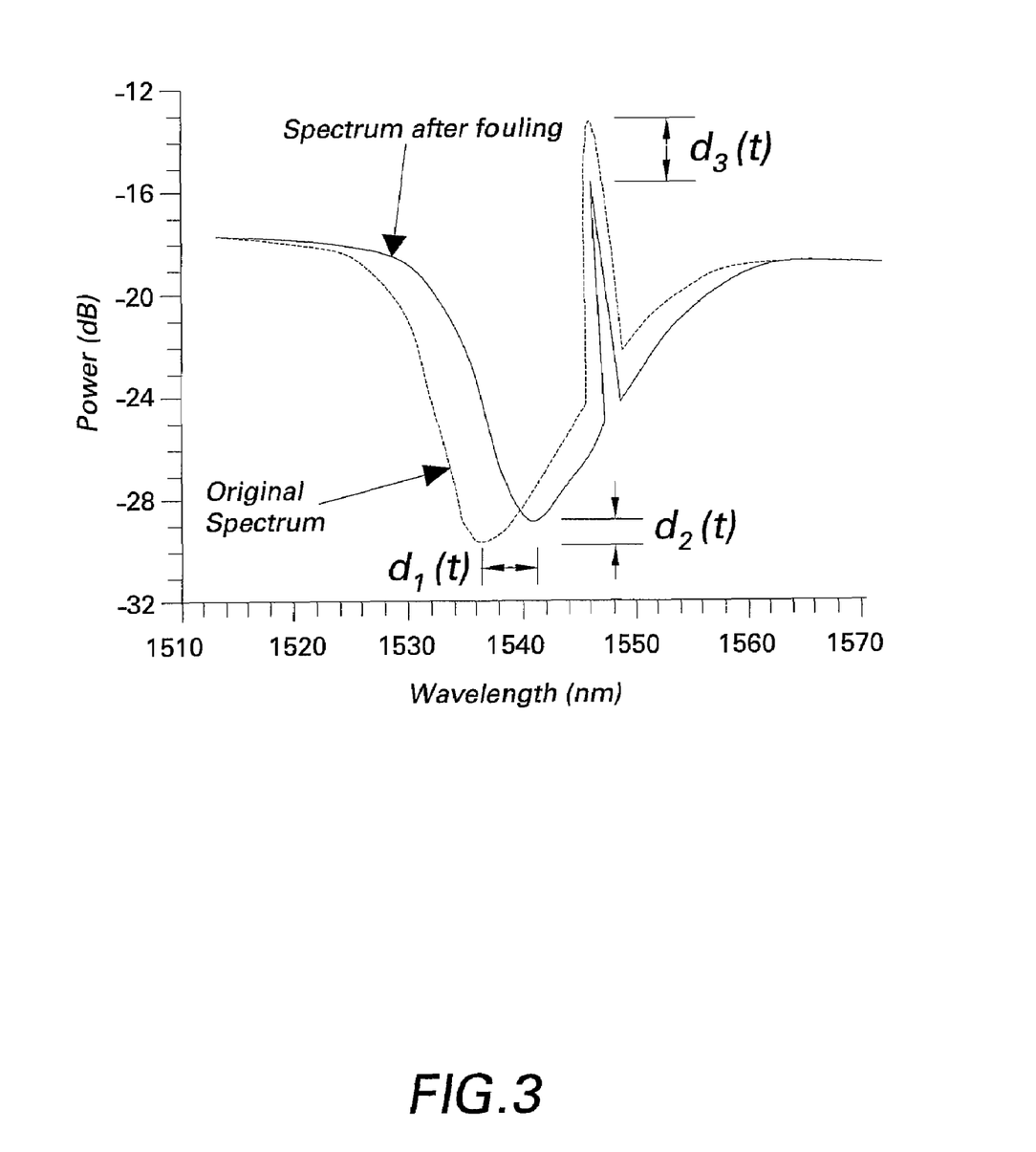
FIG. 3 is a graph depicting the change in spectrum due to fouling formation around the fiber grating sensor surface.

When a fouling layer, such as fouling layer 65, deposits on a surface of the fiber optic cable 12, the refractive index of the medium around the long period grating 14 changes. Because the refractive index of the fouling layer 65 is different from that of the bulk medium, i.e., water, from which it precipitates, the change of refractive index induced by fiber fouling produces a change in the long period grating 14 spectrum that originates from the coupling strength changes among the guided mode and cladding modes and radiation modes. When an external refractive index moves from a low-index water to a higher index inorganic fouling material, the increase in the index will shift the transmission position of the fiber sensor and its power intensity or spectral characteristics. By tracking the changes in the spectrum characteristics, mainly the change in the position ($d_1(t)$) and the intensity ($d_2(t)$) of the long period grating 14 peak and the intensity ($d_3(t)$) of the fiber Bragg grating 16 peak, fouling can be detected and these signals can be correlated to the deposit thickness, as shown in FIG. 3. Through the use of the system 10, a fouling layer 65 having a thickness no greater than one micron can be detected.

Figure 2:
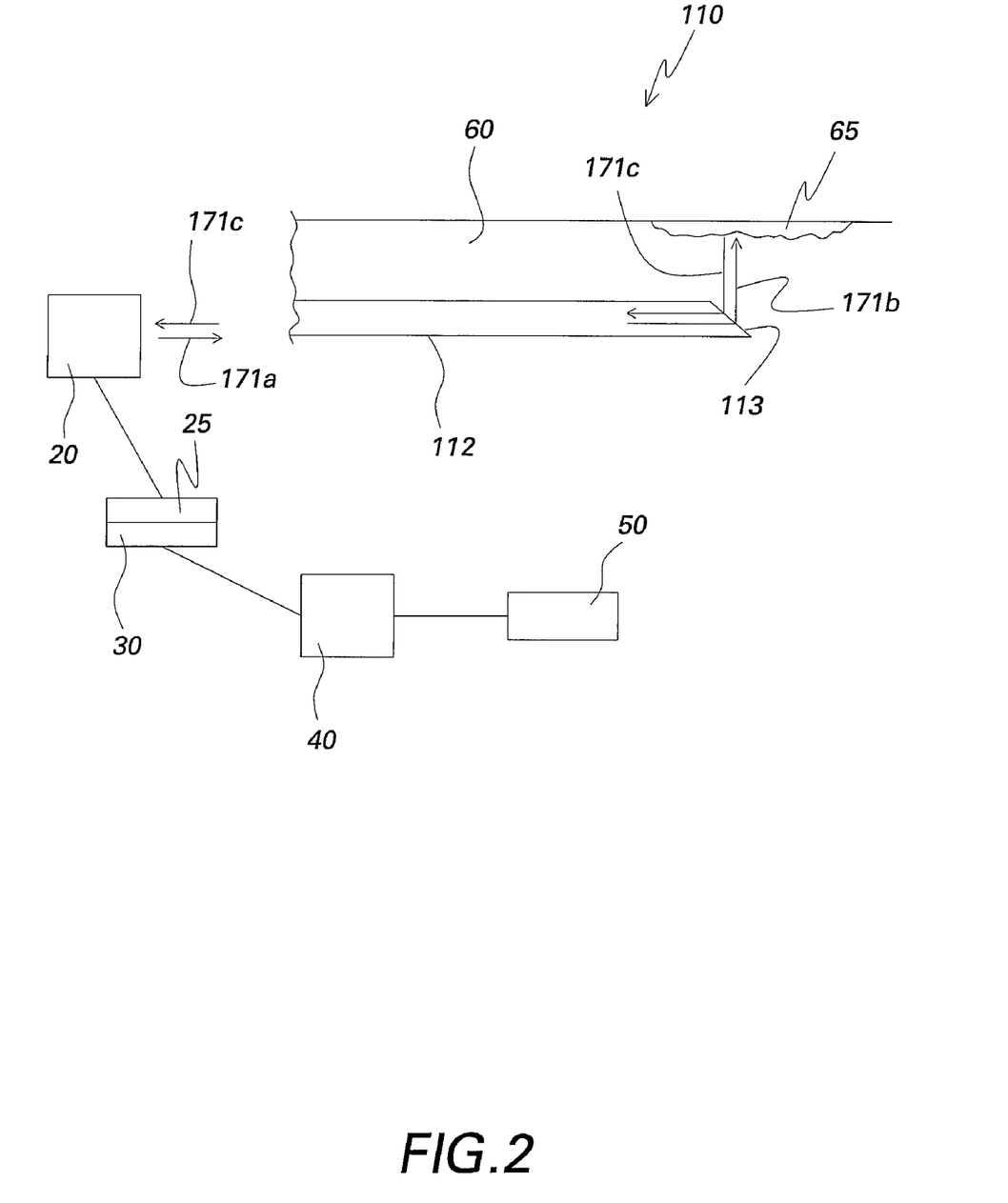
FIG. 2 is a schematic depiction of another interferometer-based system constructed in accordance with an embodiment of the invention.

Referring now to FIG. 2, there is shown a fouling inspection system 110 that includes a fiber optic cable 112, a light source 20, an interferometric spectrometer 25, a photo detector 30, signal conditioning circuitry 40, and a central processing unit 50. The fiber optic cable 112 does not include a long period grating or a fiber Bragg grating as in the fiber optic cable 12 described with reference to FIG. 1. Instead, the fiber optic 112 includes a facet edge 113 at which light signals are reflected. The facet edge 113 may be uncoated, or it may be coated with a reflective material, such as, for example, gold. Specifically, a light signal 171a is transmitted through the fiber optic 112. At the facet edge, the signal 171a is reflected, and the reflected signal 171b is transmitted through the cladding 60 toward a fouling layer 65. A portion 171c of the reflected signal 171b is reflected back to the facet edge and into the fiber optic cable 112 to be analyzed by the interferometric spectrometer 25 and the photo detector 30.

While the inspection systems 10, 110 have been described in terms of reflected signals, it should be appreciated that instead of reflecting signals back through the fiber optic cable 12, 112 to the interferometric spectrometer 25 and photo detector 30, the signals may be transmitted through the fiber optic cable 12, 112 and to an optical coupler (not shown). Alternatively, the signals may be transmitted through the fiber optic cable 12, 112 to a second photo detector, such as photo detector 31, and a second interferometric spectrometer 27 (FIG. 1). In another embodiment, some signals may be reflected back to the interferometric spectrometer 25 and photo detector 30 while other signals may be transmitted on to the interferometric spectrometer 27 and the photo detector 31.

Figure 4:
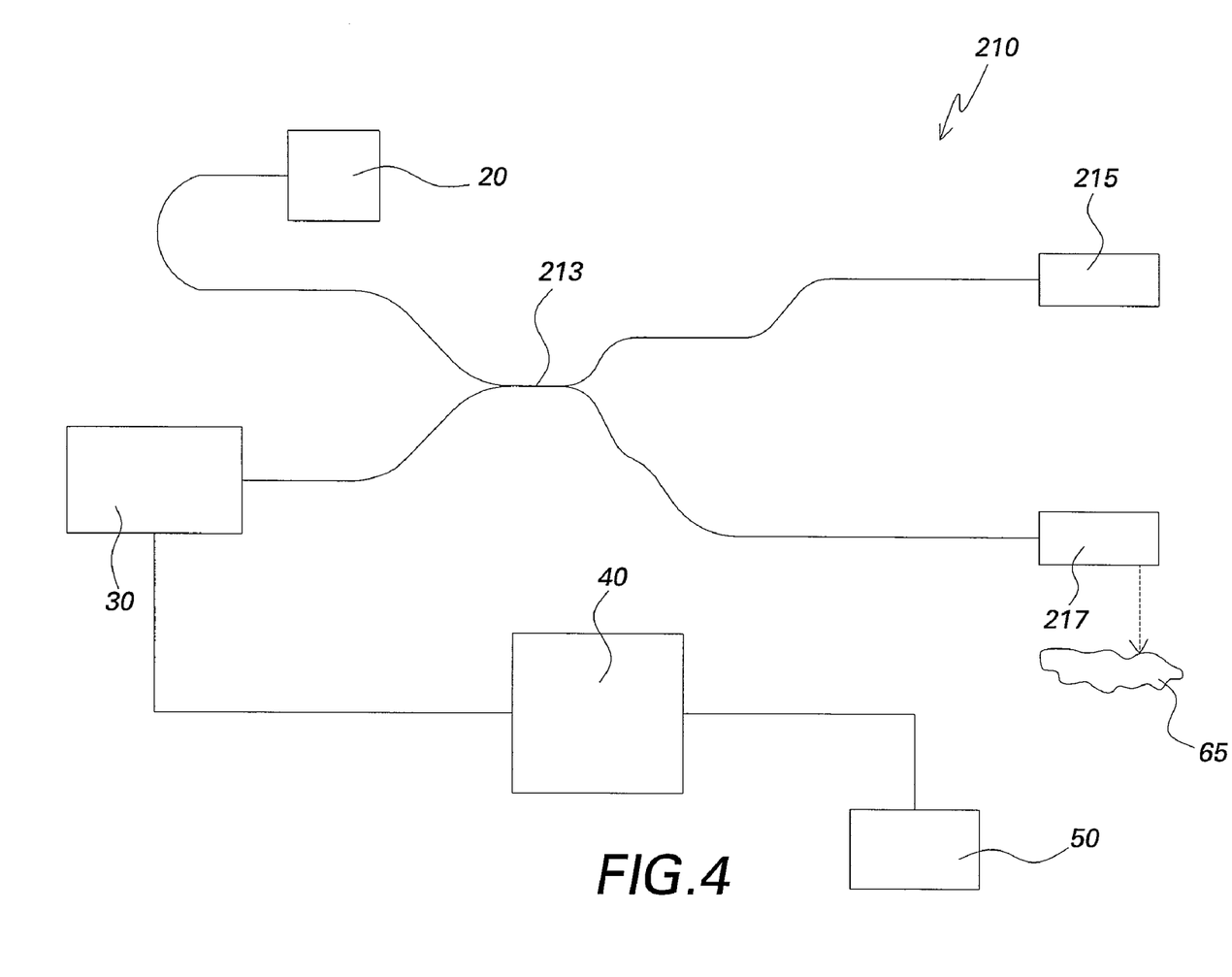
FIG. 4 is a schematic depiction of another interferometer-based system constructed in accordance with an embodiment of the invention.

FIG. 4 illustrates a fouling inspection system 210. The system 210 utilizes optical coherence tomography (OCT) to obtain millimeter deep sample penetration with micron level axial and lateral resolution. The system 210 includes a light source 20, a photo detector 30, signal conditioning circuitry 40, and a central processing unit 50. Further, the system 210 includes a fiber coupler 213, a reference probe 215, and a sample probe 217.

The light source 20, which may be a broadband light source such as a superluminescent diode, is used in conjunction with a Michelson interferometer including the fiber coupler 213, the reference probe 215 and the sample probe 217, and the photo detector 30. The signal conditioning circuitry 40 is used for generating different profiles of a sample. The light generated by the light source 20 is split into two arms by the fiber coupler 213. One arm includes the reference probe 215, which includes a mirror. The other arm includes the sample probe 217. If light from both arms travels the same optical path length or optical paths with a difference of length less than a coherence length, the backscattered light from the sample arm and reference light from the reference arm will interfere to create a fringe pattern. By scanning the mirror in the reference arm, a reflectivity profile of the sample can be produced. This is considered time domain OCT. Areas of the sample that reflect back a large amount of light, for example interfaces having mismatched refractive indices, will create greater interference than areas that do not. Any light outside the short coherence length will not create interference.

Figure 5:
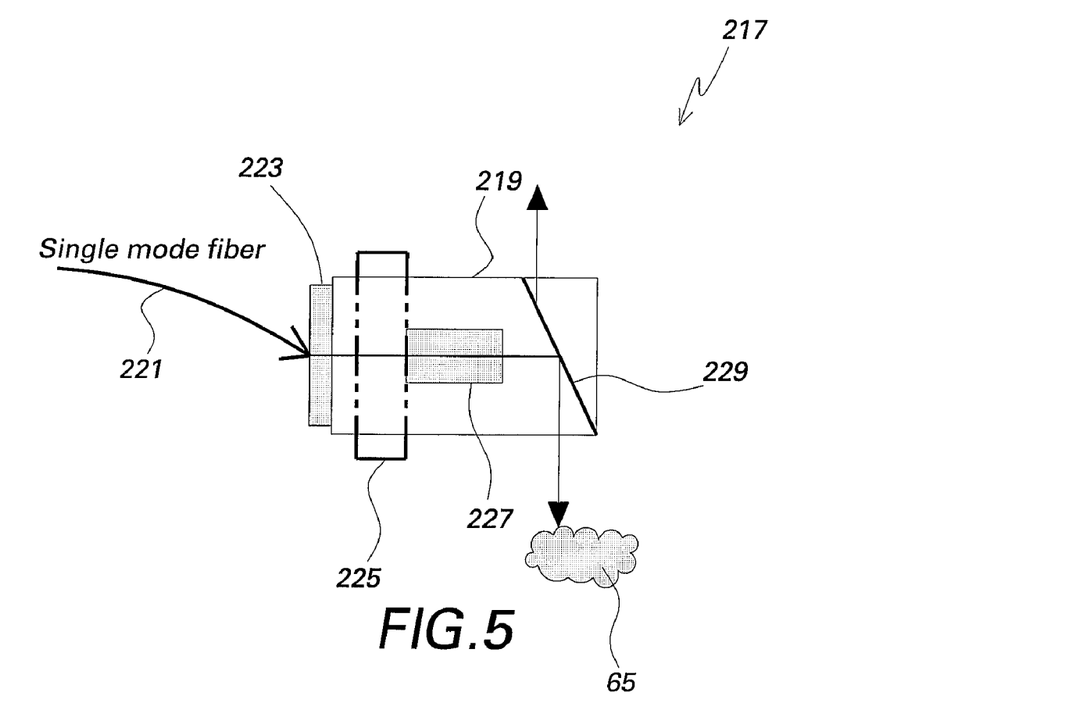
FIG. 5 is schematic depiction of the probe used in the interferometer-based system of FIG. 4.

With specific reference to FIG. 5, the sample probe 217 is shown in greater detail. The sample probe 217 includes a lens tube 219 that houses an objective lens 227. Light is transmitted into the lens tube 219 via a single mode fiber 221. The transmitted light enters the lens tube 219 through a single mode fiber adapter 223. An extending tube 225 is positioned to adjust the focus of the objective lens 227, which serves to converge the light onto the fouling layer. At the mirror 229, which may be a periscope, the light is redirected toward the fouling layer and then the reflected light from the fouling layer 65 is redirected by the mirror 229 to the objective lens 227.

Figure 6:
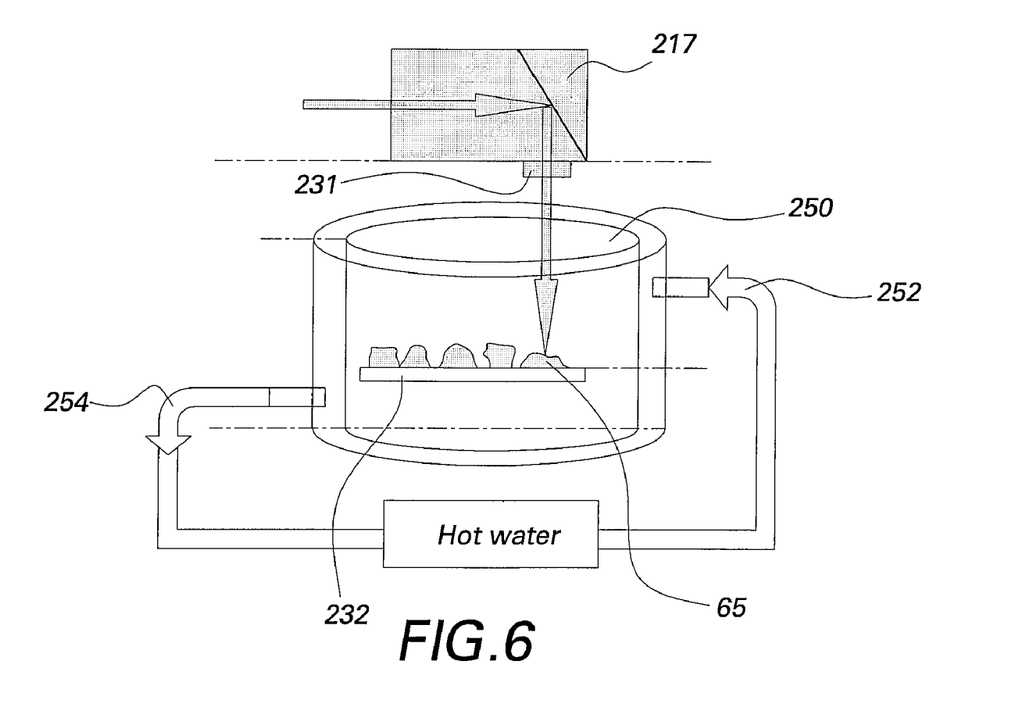
FIG. 6 illustrates the use of the probe of FIG. 5 in an underwater application in accordance with an embodiment of the invention.
Figure 7:
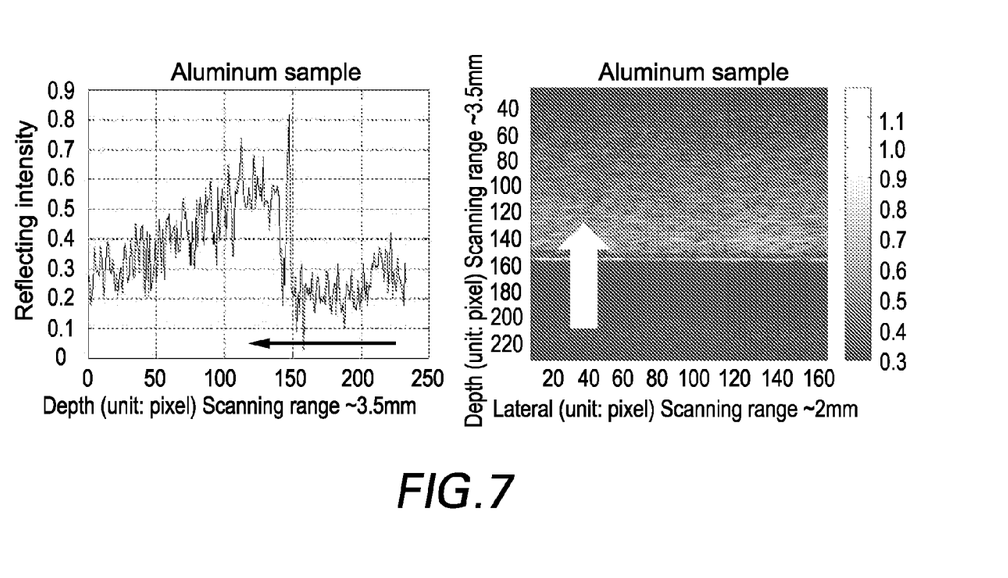
FIG. 7 illustrates a cross-sectional scan and micrograph of a brass coupon coated with a calcite layer over a polymeric deposit. The arrows indicate the direction of light probing and scanning.
Figure 8:
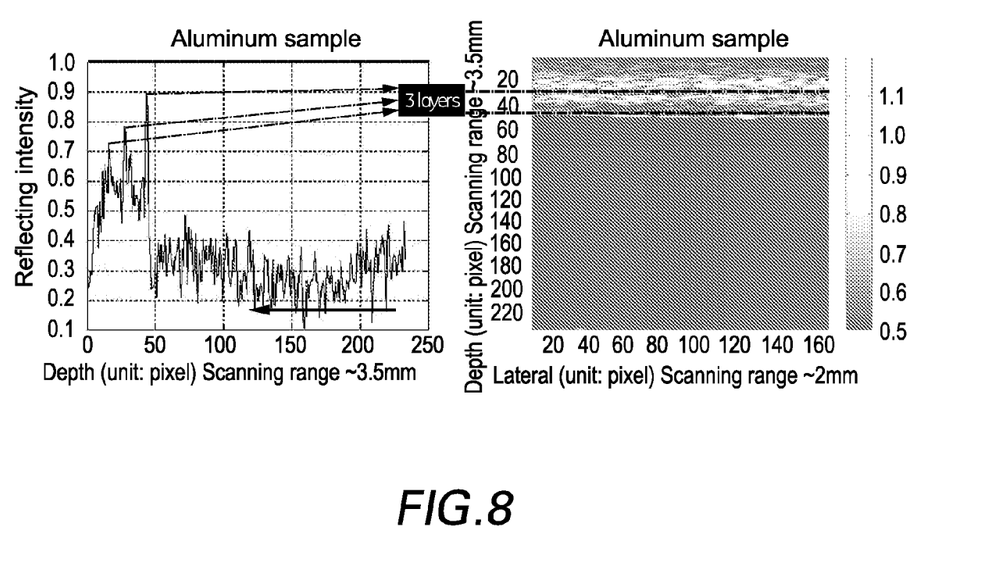
FIG. 8 illustrates a cross-sectional scan and micrograph of a copper coupon coated with a calcite layer over a polymeric deposit. The arrows indicate the direction of light probing and scanning.
Figure 9:
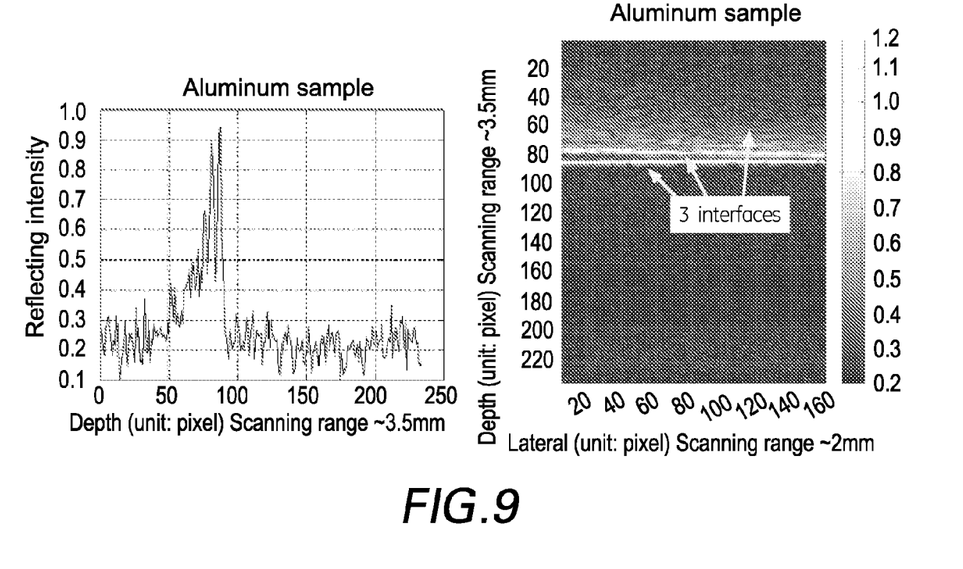
FIG. 9 illustrates a cross-sectional scan and micrograph of a stainless steel coupon coated with a calcite layer over a polymeric deposit. The arrows indicate the direction of light probing and scanning.
Figure 10:
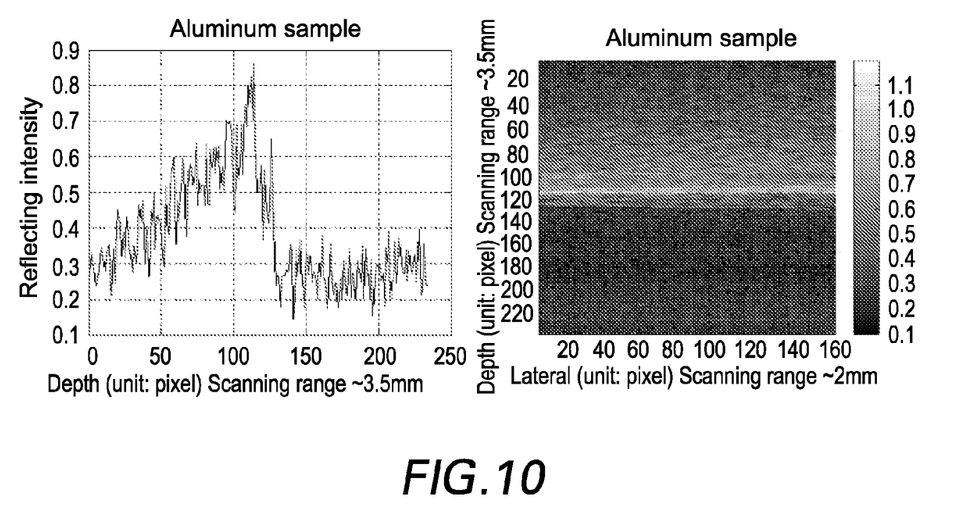
FIG. 10 illustrates a cross-sectional scan and micrograph of a corroded stainless steel coupon coated with a calcite layer.

FIG. 6 depicts the use of the sample probe 217 in an underwater application. Experiments were performed using the arrangement as depicted in FIG. 6. An optical window 231 is used to shield the probe but still transmit light to fouling layer. Specifically, numerous coupons 232 were positioned relative to the sample probe 217. The coupons 232 were made of different materials, including carbon steel, copper, corroded carbon steel, stainless steel, aluminum, and brass. Various combinations of fouling layers and multilayers, such as, for example, PMMA (polymethyl methacrylate), biofilm, calcite, were deposited onto the coupons 232 to test the feasibility of detecting the fouling layer 65 and of measuring its thickness at different depths from the external sample surface. Results of the experiments are illustrated in FIGS. 7-10.

Figure 11:
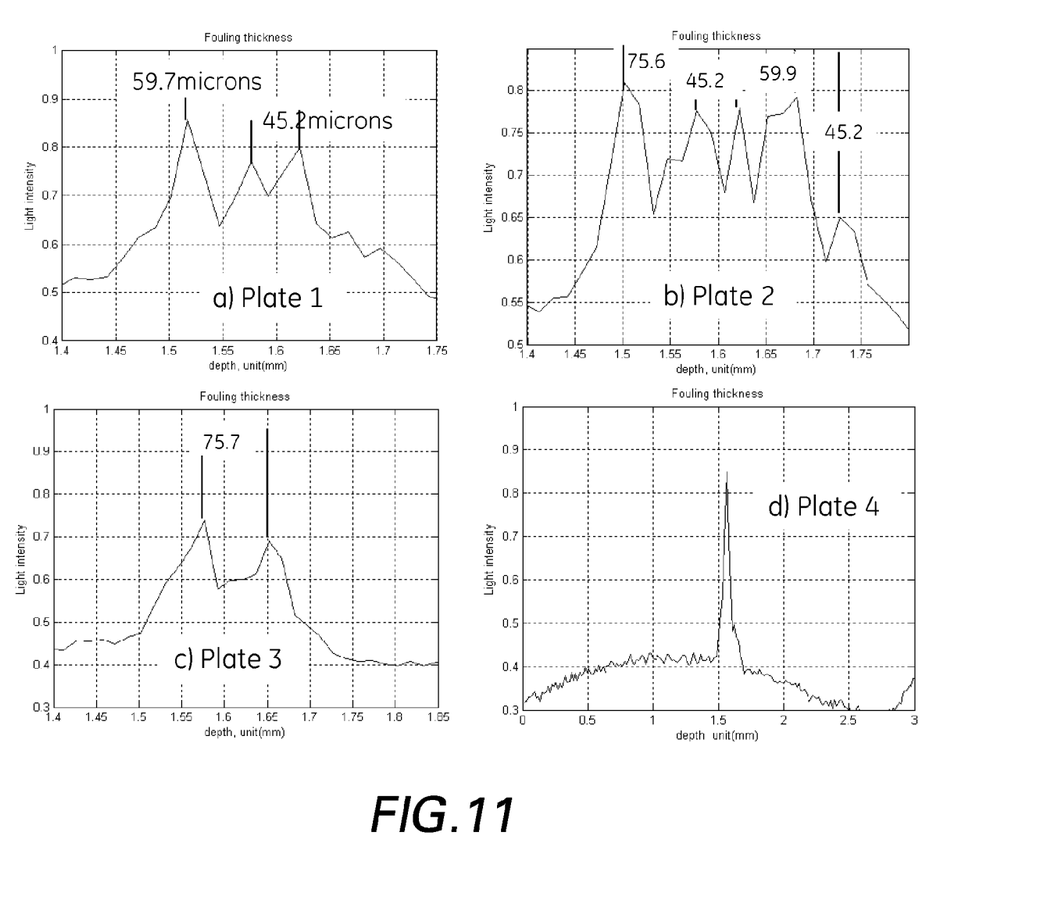
FIGS. 11(a)-(d) are cross-sectional real-time scans of carbon steel coupons exposed to creek water for three hours while maintained at 42° C.
Figure 12:
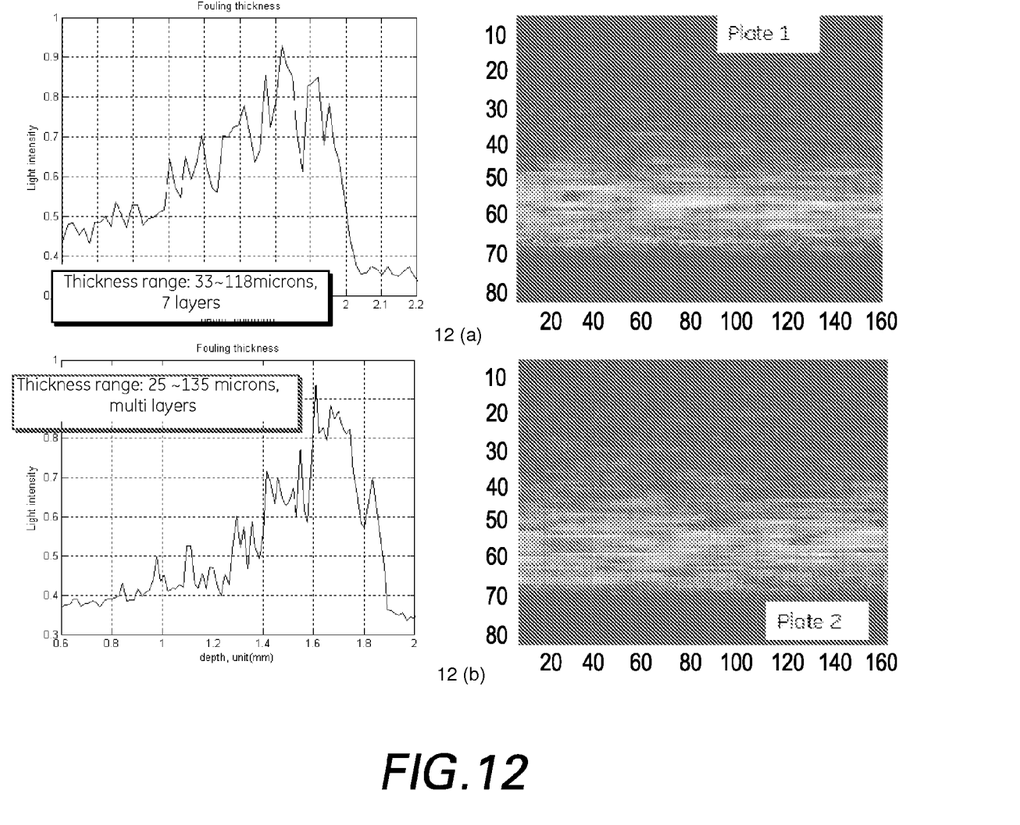
FIGS. 12(a) and 12(b) are cross-sectional real-time scans of carbon steel coupons exposed to creek water for forty-eight hours while maintained at 42° C.

The system 210 may also be used as a real time fouling detector. Referring to FIGS. 11(*a*)-(*d*) and FIGS. 12(*a*) and 12(*b*), the scans indicate the growth of fouling layers having different thicknesses and perhaps different compositions. Each of the plates 1-4 corresponds with a respective material from which a respective coupon is formed. Specifically, plate 1 corresponds to a corroded carbon steel coupon, plate 2 corresponds to a carbon steel coupon, plate 3 corresponds to a copper coupon, and plate 4 corresponds to a brass coupon. If the system 210 is suitably connected with a spectrum analyzer that can characterize materials in advance, the composition of the various fouling layers can be determined. To appropriately characterize, a calibration run on a standard with well-known concentrations should be performed before doing these measurements in the real world.

Figure 13:
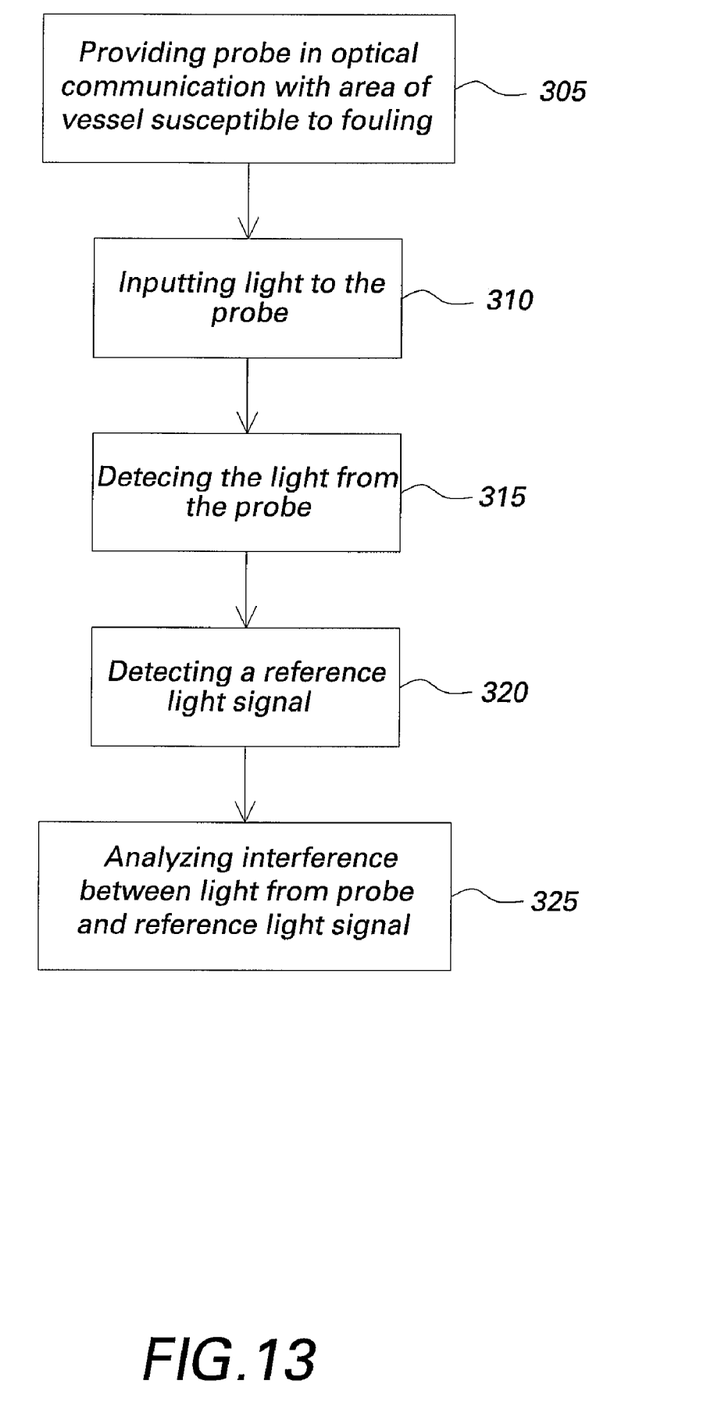
FIG. 13 illustrates a process for detecting fouling in accordance with an embodiment of the invention.

Referring now to FIG. 13, there is shown a process for detecting fouling within a vessel. At Step 305, a probe is provided in optical communication with a portion of the vessel that is susceptible to the accumulation of fouling layers. The probe may be, for example, the fiber optic 12 (FIG. 1), 112 (FIG. 2) or the sample probe 217 (FIG. 4). The vessel may be, for example, biological systems, heat exchangers, cooling towers, fractionation towers, boilers, reboilers, debutanizer, and depropanizers. The area susceptible to fouling may be, for example, a boiler or heat exchanger tubes.

At Step 310, light is input to the probe. The light may be transmitted from a broadband light source, such as, for example, a superluminescent diode. At Step 315, light is detected from the probe. The detected light may be reflected or scattered light from fouling layer 65. At Step 320, a reference light signal is detected. The reference light signal may be reflected light and it may come from, for example, the mirror of the reference probe 215 (FIG. 4). At Step 325, interference between the light detected from the probe and the reference light signal is analyzed. Through such analysis, the thickness and distribution of fouling can be determined. Further, extra spectrum analysis may indicate the composition of the fouling layer.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What is claimed as new and desired to be protected by Letters Patent of the United States is:

1. A system for detecting a fouling layer, comprising:
    a fiber optic cable that includes a long period grating and a fiber Bragg grating;
    a light source in communication with said fiber optic cable;
    at least one photo detector in communication with said fiber optic cable; and
    at least one interferometric spectrometer in communication with said fiber optic cable, wherein said interferometric spectrometer detects the fouling layer by tracking a change of refractive index induced by the fouling layer.

2. The system of claim 1, wherein said at least one interferometric spectrometer tracks a change in position and a change in intensity of a spectrum peak associated with said long period grating and an intensity of a spectrum peak associated with said fiber Bragg grating.

3. The system of claim 2, wherein said long period grating splits a portion of a signal from said light source into a cladding surrounding said fiber optic cable.

4. The system of claim 3, wherein said fiber Bragg grating reflects back a second portion of a signal though said long period grating.

5. The system of claim 1, comprising:
    signal conditioning circuitry in communication with said at least one photo detector; and
    a central processing unit in communication with said at least one photo detector.

6. The system of claim 1, wherein the detected fouling layer has a thickness that is less than about one micrometer.

7. The system of claim 1, wherein said fiber optic cable has a facet edge.

8. A method, comprising:
    inputting light to a probe that is in optical communication with an area of a vessel, and in which the area is susceptible to fouling;
    detecting light from the probe, which comprises detecting with an interferometric spectrometer; and, tracking a change in both position and intensity of a spectrum peak associated with a long period grating and tracking a change of intensity of a spectrum peak associated with a fiber Bragg grating;
    detecting a reference light signal; and
    analyzing interference between the light from the probe and the reference light signal.

9. The method of claim 8, wherein said probe comprises: an adapter for receiving light from said light source; a lens; a lens tube housing said lens; and a mirror, the method further comprising orienting the mirror to direct light toward a fouling layer and collecting light reflected from the fouling layer.

* * * * *